United States Patent [19]

Giarratano

[11] Patent Number: 5,078,728
[45] Date of Patent: Jan. 7, 1992

[54] DEVICE FOR RELIEF FROM MORNING SICKNESS

[76] Inventor: Robert C. Giarratano, 4632 Weston Rd., La Mesa, Calif. 92041

[21] Appl. No.: 251,691

[22] Filed: Sep. 29, 1988

[51] Int. Cl.$^5$ ............................................. A61B 17/12
[52] U.S. Cl. .................................... 606/204; 606/201
[58] Field of Search ............. 128/327, 686, 897, 898, 128/907, 329 A; 606/204, 201

[56] References Cited

U.S. PATENT DOCUMENTS

| | | | |
|---|---|---|---|
| 3,752,147 | 8/1973 | Castro et al. | 128/686 |
| 4,162,672 | 7/1979 | Yazaki | 128/1.3 |
| 4,182,338 | 1/1980 | Stanulis | 128/327 |
| 4,273,130 | 6/1981 | Simpson | 128/327 |
| 4,308,861 | 1/1982 | Kelly | 128/68 |
| 4,319,574 | 3/1982 | Sun et al. | 128/303 R |
| 4,391,270 | 7/1983 | Uragami | 128/1.3 |
| 4,479,495 | 10/1984 | Isaacson | 128/327 |
| 4,590,939 | 5/1986 | Sakowski | 128/329 A |
| 4,716,898 | 1/1988 | Chauve et al. | 128/327 |

FOREIGN PATENT DOCUMENTS 2566660  1/1986  France ............................ 128/329 A

OTHER PUBLICATIONS

Clipping from the Journal of The Royal Medical Society of Great Britain entitled "Research on Traditional Chinese Acupuncture-Science or Myth", Oct., 1988.

West Marine Products, Watsonville, Calif. 95077, Holiday Gift Guide 1989, p. 20, advertisement of "Sea Bands".

Primary Examiner—Lee S. Cohen
Assistant Examiner—Krista M. Pfaffle
Attorney, Agent, or Firm—Juettner Pyle & Lloyd

[57] ABSTRACT

A method of alleviating morning sickness in pregnant women resides in the application of a continuum of a controlled amount of pressure to the Neiguan acupressure points on both forearms of the patient. This is achieved by the use of a pair of pressure applying devices, each of which is adapted to be secured to a respective one of the patient's forearms.

Each such device comprises a strap of a length to encompass forearms of various girths, a protuberance on the strap for localized engagement with the Neiguan point on the patient's forearm, and adjustable securements on the strap for adjustably securing the strap about the patient's forearm with said protuberance engaging the Neiguan point and for adjusting the amount of pressure applied about the arm and onto said point.

3 Claims, 1 Drawing Sheet

DEVICE FOR RELIEF FROM MORNING SICKNESS

TECHNICAL FIELD

The present invention relates to the malady suffered by pregnant women, particularly in the early months of pregnancy, known as "morning sickness", and particularly to relief from this malady.

BACKGROUND ART

Morning sickness comprises nausea and vomiting, and/or related physical distress, that occurs in pregnant women on or shortly after rising in the morning, especially during the earlier months of pregnancy. Though still called "morning sickness", the onset of nausea in many pregnant women can occur at almost anytime of the day, or it can be substantially constant for days, weeks or even months.

For most women, the distress of morning sickness is sufficiently severe that they are essentially incapacitated. Every woman who has suffered through "morning sickness" does not want it to happen again, ever.

I have discovered that the application of a continuum of a controlled degree of pressure, utilizing a technique called acupressure, to a particular point or points on the body, will afford the majority of women relief from morning sickness.

Acupressure is a technique derived from acupuncture, the original Chinese practice of puncturing the body with needles at predetermined key points or locations to cure disease or relieve pain. Acupressure is a related practice, not involving puncture of the skin, wherein relief from pain may be obtained by applying pressure to selected key points or locations on the human body.

One such point, known as the Neiguan point, which is located on the flexor side of the forearm just above the wrist, has been utilized in the practice of acupuncture and/or acupressure as an application point for the alleviation of discomfort and pain. Studies conducted at hospitals in Great Britain to test the efficacy of short term, manual application of pressure to this point on pregnant women have indicated that temporary relief from morning sickness may be obtained in a significant number of cases.

Quite recently, elastic bands with pressure applying buttons secured to the elastic have been advertised and sold for use in applying pressure to the Neiguan points on a person's forearms for the purported purpose of alleviating motion sickness. To the best of my knowledge, the concept has not been used prior to my invention to alleviate morning sickness in pregnant women. In particular, elastic bands are too uncomfortable for pregnant women to wear; they are not adjustable; they fit only a limited range of arm sizes, and do not accomodate the weight and size changes many women undergo during pregnancy; they interfere with blood circulation, which of course should be avoided during pregnancy; and they cannot be worn for any extended period of time. In general, therefore, elastic bands are quite unsuited to use during pregnancy.

DISCLOSURE OF THE INVENTION

In the case of pregnant women who suffer from "morning sickness", I have discovered that the application of a continuum of controlled or moderated pressure to the Neiguan acupuncture points on both arms of the patient will result in relief of the patient's nausea, vomiting, and related physical distress. While my practice of this technique cannot presently be said to be 100 percent successful, almost all pregnant patients so treated have enjoyed a significant degree of relief from the malady, and in the majority of cases the relief is complete or substantially so.

To facilitate convenient practice of the described technique, the invention provides a very simple device comprising a strap with a self contained pressure bead or protrusion so that the patient can apply such a strap to each of her arms with the bead or protrusion engaging the Neiguan point and then pull the strap into firm but comfortable engagement around the arm so that the strap will be retained upon the respective arm and the bead or protrusion thereon will maintain a continuum of adjustably controllable pressure against the Neiguan point so long as is necessary for the relief of physical distress from nausea and vomiting.

Further to facilitate the patient's use of the device of the invention, it is preferred that the strap be formed of a plush material for comfortable engagement with the arm of the patient, be provided at one end with a buckle so that the strap can be conveniently pulled into firm but comfortable engagement with the arm, and be provided at its opposite end with a small tab of hook material of the type sold under the trademark "Velcro" so that the strap can be simply and conveniently secured in place on the patient's arm, in any desired position of adjustment, without any difficulty by the patient herself.

It is also preferred that the pressure bead or protrusion be contained within the strap so that the same cannot be displaced or lost. Also, the protrusion is preferably located adjacent the buckle end of the strap so that the remainder of the strap will serve as an universally adjustable band for encircling essentially the entire spectrum of sizes of ladies' arms, and will accommodate substantially infinite adjustment and control over the pressure applied to the Neiguan point on the arms, so that a single model or commercial embodiment of the device will serve the entire universe of prospective or target users.

These and other features, objects and advantages of the invention will become apparent from the following detailed description, as reviewed in conjunction with the accompanying drawings.

BEST MODE FOR CARRYING OUT THE INVENTION

Figure 1:
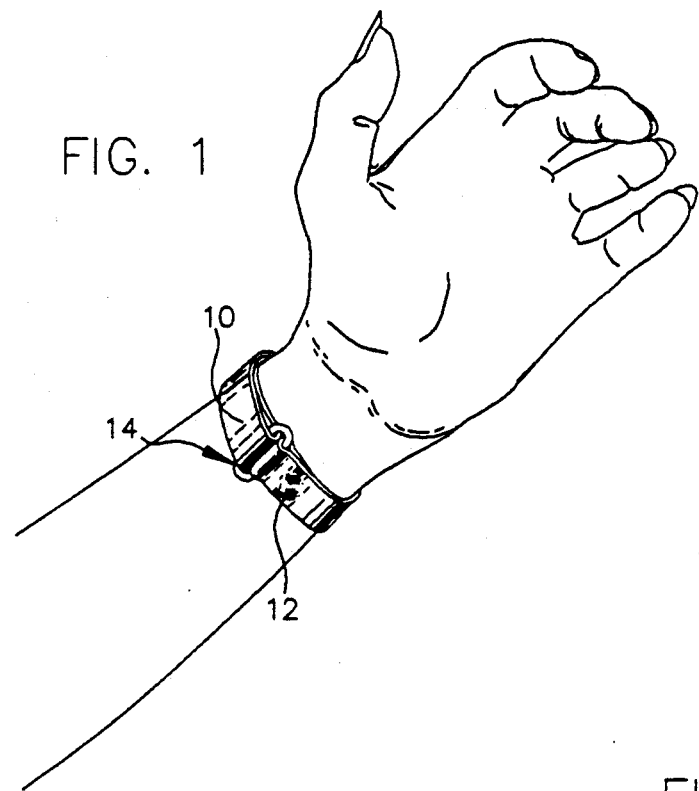
FIG. 1 is a perspective view of a preferred embodiment of the device of the invention as it would appear in use on a patient's arm.
Figure 2:
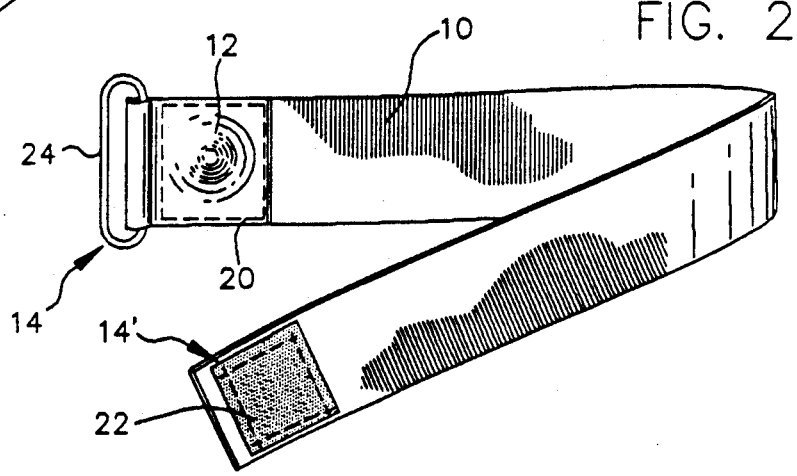
FIG. 2 is a plan view of the device with the strap folded over on itself to illustrate both the manner in which the pressure bead is contained within the strap and the manner and location in which the tab of hook locking material is secured to the strap.
Figure 3:
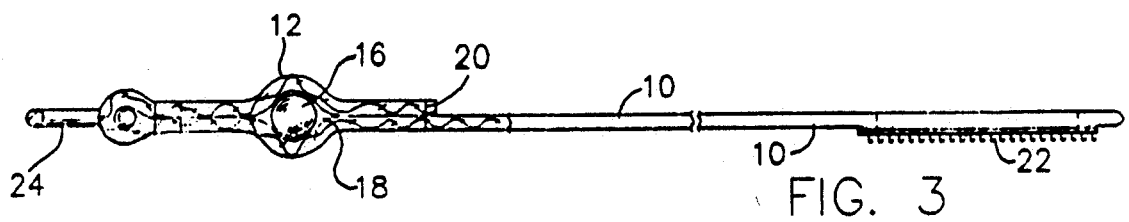
FIG. 3 is a side view, partly in cross section, illustrating the construction of the preferred embodiment of the device of the invention.

Referring to the drawings, the best mode presently contemplated by me for carrying out my invention comprises a strap 10 of a length adequate to encircle the patient's arm, a pressure applying protuberance 12 on the strap, and means 14—14' for securing the strap snugly and firmly about the patient's arm with the protuberance 12 engaging the Neiguan pressure point on the patient's arm.

As depicted illustratively in FIG. 1, the Neiguan point is located about 5 cm above the crease of the patient's wrist between the two central tendons on the flexor surface of the patient's forearm. Application of a localized, continuous, firm pressure to this point on both of the patient's forearms will in an amazingly high percentage of cases alleviate the morning sickness suffered by pregnant women.

The protuberance 12 need not be large nor project a great distance from the surface of the strap to achieve the stated purpose. All that is needed is a relatively unyielding projection that will bring pressure to bear specifically on the Neiguan point. In the preferred embodiment, the protrusion or projection 12 is formed by a non-yielding pressure applying element in the form of a hard spherical bead 16 about 1 cm in diameter that is contained within the strap. To ensure the patient's comfort, and also to ensure against displacement or loss of the pressure applying element, the bead 16 is preferably secured within a closed pocket 18 that is formed by folding the strap back upon itself and stitching or otherwise securing the folded portions of the strap together about the bead 16, as indicated at 20. Other forms of pressure applying elements, such as a cylindrical rod and/or a self contained rib formed on the strap, may be substituted for the bead as desired, provided of course that a Neiguan contacting projection or protuberance 12 is formed on the strap.

The strap 10 is preferably made of a nonelastic, plush surfaced material so that the same may be worn without discomfort by the patient for several hours, days, weeks, or even months, as may be required according to the severity and longevity of the malady suffered by a particular patient. Also, use of a plush material capable of locking engagement with a self locking hook material of the type sold under the trademark "Velcro" facilitates convenient, universal, adjustable securement of the strap about the patient's arm, and thus substantially infinite adjustment of the amount of pressure applied onto the Neiguan point, to the personal preference, need and/or tolerance of the individual patient. Such adjustability also insures against interference with the patient's blood circulation. Thus, for the purpose of universal adjustability of the strap, one or more tabs 22 of "Velcro" hook material are stitched or otherwise secured to the surface of the strap 10.

Use of the "Velcro" hook type of locking tab or tabs with a strap formed entirely of plush surfaced or hook receptive material facilitates manufacture of a single, universal model of the device of the invention that is adaptable to the entire target audience, i.e., to substantially the entire spectrum of sizes of women's forearms that may be encountered in the practice of obstetrical care. For this purpose, in the preferred embodiment of the invention, the strap is suitably about 2 ½ cm wide and about 28 cm long in its finished form as illustrated in the drawings. With the specific securement means 14—14' illustrated and about to be described, this arrangement results in universal adaptability of the device to ladies' forearms having a circumferential measurement or girth of any where from about 7 cm up to about 23 cm, and also provides for individual adjustment of the degree of pressure applied to the forearm and the Neiguan point throughout this entire spectrum of forearm girths.

Because the device of the invention may have to be worn by patients for hours, days, weeks or even months, depending upon the severity and/or longevity of suffering, it is important that the securement means 14—14' be capable of maintaining the device in secure and fixed position on a lady's forearms for prolonged periods of time and yet be readily and easily adjustable, removable, and remountable so that the patient herself can mount, adjust and remove the device on each of her arms as needed or desired. To achieve all of the above stated objectives, the securement means 14—14' in the preferred embodiment of the device is comprised of a combination of (i) a strap 10 which throughout its length presents a surface of plush material suitable for interlocking reception of (ii) a tab 22 of "Velcro" locking hook material secured to one end of the strap, and (iii) a buckle 24 at the other end of the strap through which said one end of the strap may be threaded and folded back on itself to bring the tab 22 into locking engagement with the plush surface of the strap 10.

By virtue of the described construction, a single model of the device of the invention will fit both the right and left arms of target patients of practically all sizes.

The buckle 24 is preferably located adjacent the protuberance or projection 12 so that the buckle will be located on the interior or flexor surface of the forearm when the device is in use, thus to be less obstrusive when the device is being worn, and also to accomodate adjustable tightening of the strap throughout the full range of about 7 to 23 cm as previously described. To facilitate economical manufacture of the device, the end of the strap 10 to which the buckle 24 and the bead 16 are to be secured is first threaded through the buckle and folded back on itself and then stitched to form the pocket 18, thereby to define a pivotal mounting for the buckle at the end of the strap and a pocket next adjacent the buckle for reception of the pressure applying element 16. The hook material tab 22 is secured to the opposite end of the strap, preferably on the surface thereof opposite that of the folded back portion of the strap at the buckle end of the strap. Thus, when the device is worn, the folded back or pocket portion of the strap will be on the arm engaging side of the strap so that such portions of the strap will be less obtrusive aesthetically when the device is being worn.

For purposes of identification, individualization and/or aesthetics, a surface portion of the strap on the side thereof opposite the locking tab 22 may bear a trademark, or an identification tag, or some form of aesthetic ornamentation that would serve to individualize the device to the particular patient. Also, the strap could be ornamented or shaped to selected ornamental designs to make the same look more like a ladies' ornamental bracelet than a distress relieving device, all without sacrifice of the advantageous benefits of the invention.

Thus while a preferred embodiment of the invention has been illustrated and described, which embodiment accomplishes all of the objectives of the invention in a convenient, economical and facile manner, it will be appreciated that various changes, rearrangements and modifications may be made therein without departing from the scope of the invention, as defined by the appended claims.

I claim:

1. A bracelet for use in alleviating morning sickness during pregnancy by applying a continuum of a controlled amount of pressure to the Neiguan acupressure points on the forearms of the wearer, comprising an essentially non-elastic strap of a length to encircle forearms of various girths and having plush hook receptive surfaces over substantially its full length, a buckle adjacent one end of said strap, said one end of said strap extending through said buckle and being folded back on itself to connect said buckle to said one end of said strap, said one end of said strap being folded back on itself a distance sufficient to form a pocket between the two layers of said strap adjacent said buckle, a pressure applying bead in said pocket, the two layers of said strap adjacent said buckle being secured to one another about said bead to secure said buckle to said one end of said strap and to secure said bead within said pocket in said one end of said strap adjacent said buckle, the other end of said strap being threaded through said buckle and folded back on itself to mount said strap on the wearer's forearm with said bead in engagement with the Neiguan acupressure point on the wearer's forearm, said other end of said strap being adjustable relative to said buckle to accomodate adjustment of said strap about forearms of various girths and to adjustably control the amount of pressure applied by said bead to said acupressure point, and a tab of self locking hook material on the folded back portion of said other end of said strap engageable with the plush surface of the underlying portion of said strap, said tab lockingly engaging the plush surface of said strap at practically any location throughout substantially the full length of said strap after the strap has been adjustably tightened about the wearer's forearm for firmly securing said strap in adjusted position on the wearer's forearm with said bead engaging said acupressure point and applying a continuum of a controlled amount of pressure to the point.

2. A bracelet as set forth in claim 1, wherein said bead is an essentially nonyielding sphere having a diameter of about 1 cm.

3. A bracelet as set forth in claim 1, wherein said strap is about 2½ cm wide and about 28 cm long.

* * * * *